United States Patent [19]

Dobberstein et al.

[11] 4,361,697

[45] Nov. 30, 1982

[54] **EXTRACTION, SEPARATION AND RECOVERY OF DITERPENE GLYCOSIDES FROM *STEVIA REBAUDIANA* PLANTS**

[75] Inventors: Robert H. Dobberstein, Wheaton, Ill.; Mohamed S. Ahmed, Cairo, Egypt

[73] Assignee: F. K. Suzuki International, Inc., Arlington Heights, Ill.

[21] Appl. No.: 265,905

[22] Filed: May 21, 1981

[51] Int. Cl.³ .............................................. C07H 1/08
[52] U.S. Cl. .................................... 536/128; 536/127
[58] Field of Search ........................................ 536/4, 1

[56] References Cited

U.S. PATENT DOCUMENTS

| | | | |
|---|---|---|---|
| 3,723,410 | 3/1973 | Persinos | 536/4 |
| 4,082,858 | 4/1978 | Morita et al. | |
| 4,109,075 | 8/1978 | Deaton | 536/4 |
| 4,171,430 | 10/1979 | Matsushita et al. | 536/4 |
| 4,256,875 | 3/1981 | Gabriel et al. | 536/4 |

OTHER PUBLICATIONS

Y. Hashimoto et al., *Shoyakugaku Zasshi* 32:209, [1978].
Y. Hashimoto et al., *J. Chromatography*, 161:403, [1978].
M. S. Ahmed et al., *J. Chromatography*, 192:387, [1980].

*Primary Examiner*—Johnnie R. Brown
*Attorney, Agent, or Firm*—Gerlach, O'Brien & Kleinke

[57] ABSTRACT

A process for recovering diterpene glycosides from the *Stevia rebaudiana* plant includes the steps of sequentially extracting plant material with a first solvent of intermediate polarity to extract plant substances which tend to interfere with a liquid chromatographic separation of the glycosides, and then with a second solvent of high polarity to extract glycosides, and chromatographically separating the extracted glycosides by introducing them onto a liquid chromatography column having a packing of an oxygen-containing organic stationary phase covalently bonded through a silicon atom to an inorganic support, eluting them with a solvent of polarity higher than that of the first solvent but lower than that of the second solvent, and collecting individually eluate fractions rich in respective glycosides.

31 Claims, 2 Drawing Figures

EXTRACTION, SEPARATION AND RECOVERY OF DITERPENE GLYCOSIDES FROM STEVIA REBAUDIANA PLANTS

BACKGROUND OF THE INVENTION

This invention relates to a process for the extraction, separation and recovery of diterpene glycosides naturally occurring in the plant *Stevia rebaudiana* Bert. Hemsl. (Compositae), herein referred to as *S. rebaudiana*.

The desire for low calorie, or no-calorie, sweeteners led originally to the use of artificial sweeteners such as the cyclamates and saccharin, as substitutes for sucrose. Questions of their effects on health having arisen, a search for other non-sucrose sweeteners is in progress. The search has turned to sweeteners of natural origin, the rationale being that they would be less likely to have harmful effects. Many natural sweeteners, however, have disadvantages relating to the taste sensations they produce, such as a low degree of sweetness or an unpleasant aftertaste. Other disadvantages may include decomposition when heated during cooking.

*S. rebaudiana*, a plant native to Paraguay, has been used as a sweetening agent. The leaves of this plant have been reported to contain at least eight structurally related diterpene glycosides (referred to hereinafter at times as DTG materials): steviolbioside, stevioside, rebaudiosides A to E and dulcoside A. Table 1 depicts their structural formulae. A number of these glycosides are sweet in taste. Stevioside, rebaudioside A and rebaudioside C (dulcoside C) are present in the largest quantities and are the sweetest of the DTG materials. Efforts have been made to recover and separate the sweetest components for commercial use as sweeteners. U.S. Pat. No. 4,082,858, issued to Morita et al., describes a process of separation and isolation of one of the sweet-tasting diterpene glycosides (rebaudioside A).

TABLE 1

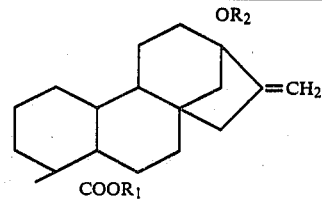

| COMPOUND | R₁ | R₂ |
|---|---|---|
| Steviolbioside | —H | —G²—¹G |
| Stevioside | —G | —G²—¹G |
| Rebaudioside A | —G | —G²₃⟨¹G / ¹G |
| Rebaudioside B | —H | —G²₃⟨¹G / ¹G |
| Rebaudioside C (Dulcoside B) | —G | —G²₃⟨¹Rh / ¹G |

TABLE 1-continued

| COMPOUND | R₁ | R₂ |
|---|---|---|
| Rebaudioside D | —G²—¹G | —G²₃⟨¹G / ¹G |
| Rebaudioside E | —G²—¹G | —G²—¹G |
| Dulcoside A | —G | —G²—¹Rh |

G = glucose
Rh = rhamnose

Generally, the prior recovery processes involve:
1. Extraction of the *S. rebaudiana* plant material with a highly polar solvent such as water or methanol to give a DTG material-containing extract.
2. Introduction of the DTG material, in a form suitable for liquid chromatography, onto a liquid chromatography column, elution with a polar solvent, and identification and separation of the eluate fraction(s) containing DTG material.
3. Removal of the eluting solvent from the fraction(s) containing DTG material.

Ordinary liquid chromatography imposes trade-offs between the factors of purity of product and quantity of product purified in a given time: the higher the purity the less the quantity of product purified per unit of time. While very large columns have been used commercially to obtain high purity at a reasonable output of product, it has been found previously that such results may be obtained in a more compact system, employing high performance liquid chromatography (HPLC) equipment, which uses high fluid pressures to drive eluting solvent continuously through very tightly-packed high surface area packing. Thus, Y. Hashimoto and his coworkers reported (Shoyakugaku Zasshi 32:209 [1978]; *J. Chromatography* 161:403 [1978]) the separation of two of the *S. rebaudiana* DTG materials, stevioside and rebaudioside A, with an HPLC system. So far as we are aware, however, no prior single liquid chromatographic system has been reported to separate all of the eight DTG materials known to be recoverable from *S. rebaudiana*. It would be desirable to effect such separation with a single system and in a unitary operation.

SUMMARY OF THE INVENTION

In accordance with the invention, a process for recovering diterpene glycosides from *Stevia rebaudiana* plant material is provided, which includes the steps of sequentially extracting *Stevia rebaudiana* plant material with a first solvent of intermediate polarity to remove impurities therefrom in a first extract substantially free of diterpene glycosides, and then with a second solvent of high polarity to give a second extract containing diterpene glycosides; chromatographing the resulting extracted diterpene glycosides on a liquid chromatography column having a packing comprising an oxygen-containing organic stationary phase covalently bonded through a silicon atom to an inorganic support, such extracted glycosides being introduced onto the column for chromatography thereon in solution in the second solvent or in another solvent having a polarity not substantially greater than the polarity of the second solvent, the column being eluted with a solvent of polarity higher than that of the first solvent and lower than that of the second solvent; and collecting individually eluate fractions rich in respective diterpene glycosides.

The foregoing overall process may be employed to recover diterpene glycosides in high yields and in high purities. The extraction steps enable a plant extract to be prepared which is rich in DTG materials and substantially free of impurities which interfere with a subsequent chromatographic separation of certain of the diterpene glycosides. The extraction steps are independently useful for obtaining diterpene glycoside concentrates, comprising mixtures of sweetening agents, useful as such or as source materials for the individual glycosides contained therein.

The chromatography enables a sharp separation of diterpene glycoside materials from each other, thus making them available in high degrees of purity. The chromatography may be employed for separating mixtures of diterpene glycosides obtained or prepared from natural or other sources, in the above-described and other ways. The chromatography may be employed both for product recovery and for analytical purposes. A particular advantage of the chromatography is that it may be employed for the separation of all of the eight diterpene glycosides known to be recoverable from *S. rebaudiana* from each other.

The process of the invention is especially well adapted to be carried out in a high performance liquid chromatography system, so as to realize the advantages of such system.

DESCRIPTION OF THE PREFERRED EMBODIMENTS

Figures 1, 2:
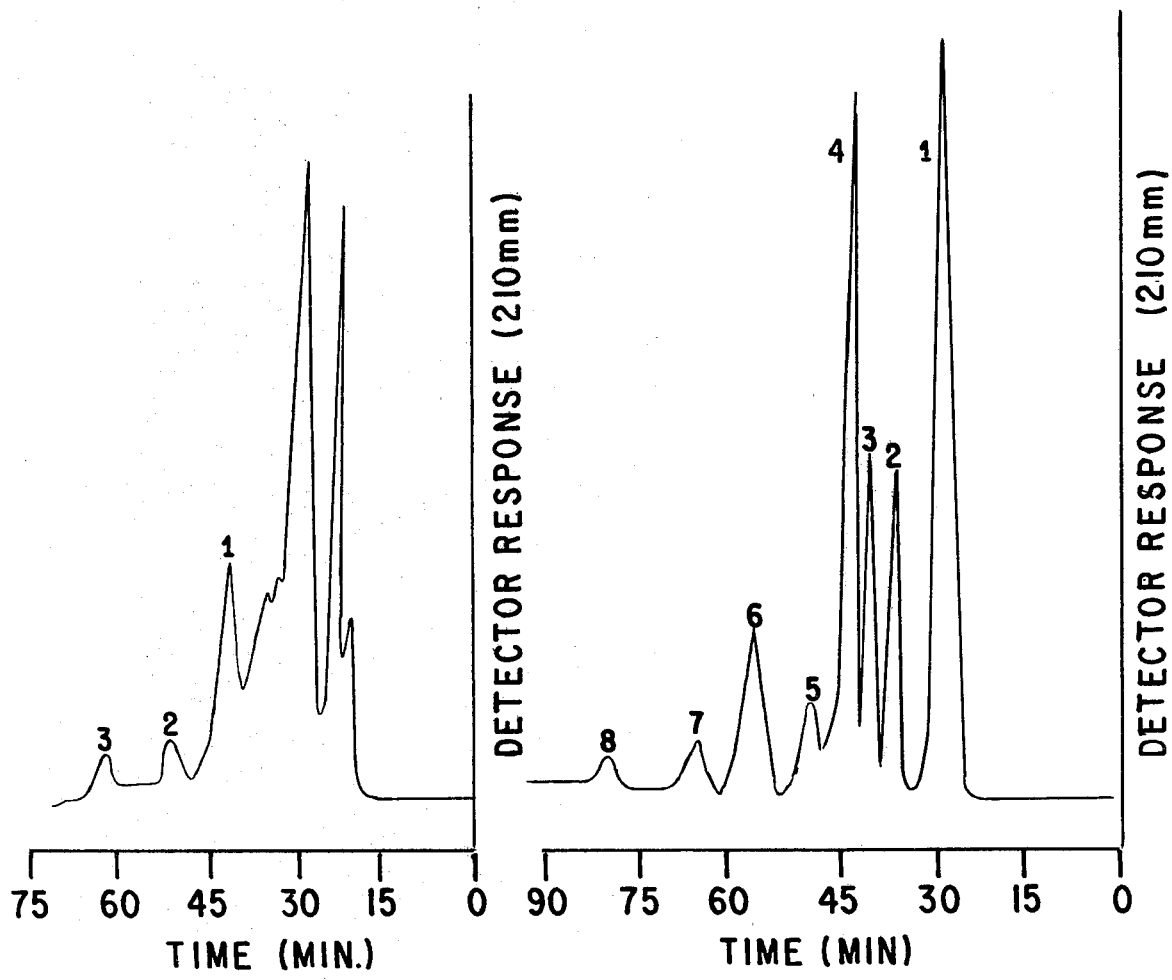
FIG. 1 is a graph illustrating the liquid chromatographic separation of diterpene glycosides present in an extract of *S. rebaudiana*, showing separation of stevioside, rebaudioside A and rebaudioside C in accordance with the invention.
FIG. 2 is a graph illustrating the liquid chromatographic separation of a mixture of stevioside, rebaudiosides A through E, steviolbioside and dulcoside A in accordance with the invention.

Diterpene glycosides (DTG materials), including sweet-tasting substances, are found in the stems, seeds and leaves of the *S. rebaudiana* plant, being present in the highest concentration in the leaves. The leaves, therefore, are the preferred starting material for recovery of diterpene glycosides from the *S. rebaudiana* plant.

Impurities or non-DTG materials present in the plant material first are removed therefrom by extraction thereof with a selective first solvent, which is a solvent for certain interfering impurities, but is substantially a non-solvent for DTG materials.

Since DTG materials are of relatively high polarity and thus are soluble in high polarity solvents such as water or lower alkanols, they can be extracted from the plant material by contacting it with such solvents. However, in addition to DTG materials, *S. rebaudiana* contains other polar materials, which also are removed by the high polarity solvents. It has been found in the invention that such non-DTG materials act as "impurities" which tend to interfere with attempts to separate individual diterpene glycosides from the mixture found in a polar solvent extract. It has been found also that a solvent of polarity lower than that of water and lower alkanols will tend to show selectivity, i.e., such a solvent will tend to selectively extract "impurities" from the plant material while not extracting diterpene glycosides.

If the extraction solvent is one of low polarity, for example an alkane such as hexane, only the lowest polarity impurities are extracted, and much of the more polar impurities remain in the marc (i.e., the insoluble residue remaining after extraction of the plant material with solvent). Therefore, the first extraction of the sequential extraction steps of the invention is carried out with a first solvent of "intermediate" polarity, i.e., of polarity less than that of water or lower alkanols but greater than that of the alkanes. The preferred solvents for the first extraction are the liquid lower haloalkanes, i.e., liquid under standard temperature and pressure conditions. Further preferred are the one to four-carbon atom haloalkanes, especially chloroform. In addition to removing relatively polar impurities, this first extraction also removes relatively non-polar plant constituents. Thus, it effectively "defats" the plant materials, making them more readily extractable by the high polarity solvents used in the second extraction, described below.

The foregoing first extraction may be carried out in conventional ways, by contacting the plant material with the solvent for a period of time at ambient or elevated temperature, and then filtering off the resulting extract. It is preferred that plant material be air dried before extraction, preferably by heating to a temperature of 50°–100° C. for a period of 0.5–2 hours. A soxhlet-type extraction is preferred, where the extraction temperature is approximately that of the solvent's boiling point. It also is preferred that the plant material be finally divided, to provide greater surface area; mesh sizes of from about 0 to about 50 (U.S. Sieve Series) are further preferred. The proportion of extraction solvent preferably is from about 10 liters to about 60 liters of solvent to one kilogram of leaves. The duration of the extraction may be from 0.5 hour to 50 hours, with a period of from about 1 hour to about 20 hours preferred.

Following the first extraction, the DTG materials and certain highly polar non-DTG materials, are removed from the plant material, i.e., the marc remaining, by a second extraction with a high polarity second solvent, to obtain maximum recovery of the DTG materials. The preferred solvents for this second extraction are lower alkanols, more preferably, having from one to three carbon atoms, especially methanol. Alternatively, the DTG materials may be removed from the plant material by extraction with water or other more highly polar solvents, to provide useful concentrates. For purposes of subsequent chromatography, however, the somewhat less polar and more volatile lower alkanol solvents are preferred, for reasons which will become evident. In general, the second extraction may be carried out in the same manner as the first extraction.

It is preferred that the purity of the solvents used in the two extractions be of practical grade, more preferably of technical grade and most preferably of ACS reagent grade, or of Fisher certified grade (Fisher Scientific Co., Pittsburgh, Pa.) or equivalent.

The individual diterpene glycosides are separated from the mixture which results from the second extraction, by liquid column chromatography. The mixture of DTG materials in a form suitable for chromatography is introduced onto a column containing a packing which tends to bind loosely (non-covalently) to it the diterpene glycosides. The strength of these bonds depends on the structure of the individual diterpene glycoside. The mixture may be supplied to the column in solution in the second solvent, which was employed for its removal from the plant material, or in solution in a third solvent, having a polarity not substantially greater than, and preferably less than, the polarity of the second solvent, as described hereinafter. An eluting solvent (the "eluent") next is passed through the column. The polarity of the eluting solvent is selected so that it tends to break the loose bonds holding the DTG material to the packing and elute (i.e., "wash out") diterpene glycosides from the packing, to give an eluate (solution of DTG material in the eluent).

It has been found pursuant to the invention that for optimum recovery of DTG materials from plant material followed by optimum chromatographic separation or resolution thereof, it is preferred that the DTG materials be supplied to the chromatography column in solution in a third solvent of polarity higher than that of the first extraction solvent yet lower than that of the second extraction solvent, and that these conditions of polarity likewise apply to the eluting solvent. The solvents are selected in this manner so as to elute the DTG materials from the column and selectively or individually in sequence. Unduly high or low solvent polarities impair resolution of the materials, and low polarities also impair recoveries from the column. Preferred third and eluting solvents are the lower alkanols, more preferably those having two to four carbon atoms, and especially 1-propanol.

In the foregoing preferred mode of operation, the second solvent, i.e., the solvent employed in the second extraction of the plant material, is removed from the extracted DTG materials and replaced by the preferred third solvent of lower polarity in a suitable manner, such as by evaporation to dryness under pressure and temperature conditions which avoid degradation of the materials, followed by dissolution of the residue in the third solvent. It has been found preferable for substantially complete dissolution of the residue to add a small minor amount of water to the preferred 1-propanol, and, in particular, to provide a solvent of 95–100% by volume of 1-propanol and the balance water. The residue is dissolved in a conventional manner, such as by stirring with the solvent at ambient temperature or with warming. The quantity of solvent required to dissolve the residue will depend upon the composition of the particular plant material subjected to extraction and thus cannot be predicted beforehand since, as is true of many natural materials, this composition is not invariable.

It is preferred, on the other hand, that the water content of the eluting solvent be no higher than 0.5% by volume, and more preferably be no higher than 0.2% by volume. Thus, optimum resolution is obtained with a minimal water content.

As set forth above, the packing of the chromatography column comprises an oxygen-containing organic stationary phase covalently bonded through a silicon atom to an inorganic support. Preferred supports are inorganic solid substances, including silica gel, silica, and alumina. Silica gel is further preferred, and especially for use in high performance liquid chromatography (HPLC) columns, microparticulate silica gel being employed most advantageously.

The stationary phase is tightly bound to the surface of the support material, and it is the component of the packing which is effective in causing a separation of the DTG materials supplied to and eluted from the column. The ability to cause separation depends on the relative abilities of the stationary phase to form a loose bond with the DTG materials and of an eluent to break such bond and, in general, is unpredictable.

It has been found, in accordance with the present invention, that an oxygen-containing organic stationary phase is effective to cause a sharp separation of DTG materials, so that individual materials may be recovered in high purities and yields. The stationary phase preferably contains an ether oxygen, i.e., at least one oxygen atom bonded in an ether linkage. Further preferred for providing the stationary phase is the glycerylpropyl moiety or radical, and it is contemplated that its precursor the glycidoxypropyl moiety also may be employed. Such moieties may be represented as bonded to the support through a silicon atom as follows:

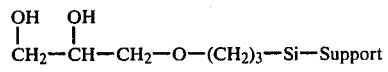

Glycerylpropyl

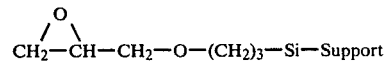

Glycidoxypropyl

Techniques for preparing such packings are described in U.S. Pat. Nos. 3,722,181 and 3,983,299. A preferred packing is that of the "Protein I-125" column (Waters Associates, Milford, Mass.), a packing of glycerylpropyl moiety covalently bonded through a silicon atom to micro-particulate silica gel having a mean particle size diameter of 10 microns and a mean surface area of 300–350 square meters per gram. Examples of other packing of glycerylpropyl moiety covalently bonded through a silicon atom to a silica support are Syn Chropak GPC 100 (Syn Chrom, Inc., Linden, Ind.) and Li Chrosorb DIOL (EM Labs., Cincinnati, Ohio).

The chromatography preferably is conducted in a high performance liquid chromatography system. The solution of DTG materials in the second or third solvent is introduced into the eluent stream at one end of the column, and eluate fractions containing the separated diterpene glycosides are removed at the other end of the column. The eluent flow rate and pressure are dependent upon the physical characteristics, e.g., packing particle size and density, and column diameter and length, of the particular system used. The temperature at which the chromatography is carried out is preferably in the range of from about 10° to about 40° C. Alternatively, but less advantageously, the chromatography may be carried out by conventional relatively low pressure methods.

The presence of DTG materials in the eluate is detected and the quantities of the materials are determined by conventional means, such as refractive index measurements or absorption in the infrared or ultraviolet (UV) regions of the spectrum. The diterpene glycosides have an absorbance at 210 nanometers (nm) in the ultraviolet region. When 1-propanol, which is transparent at this wavelength, is the eluent, a UV spectrophotometer can be used as the detector. The fractions of the eluate rich in respective DTG materials are collected individually. These fractions may be used as such, or the eluent may be removed by suitable means, such as evaporation. The diterpene glycosides isolated in this manner may, if desired, be further purified by suitable means.

An individual diterpene glycoside in a plant extract may be tentatively identified by comparing its retention time (the time elapsed between the introduction of a chromatography sample onto a column, and the appearance, in the eluate, of the diterpene glycoside in question) with the retention times found for authentic, known diterpene glycosides chromatographed under the same conditions. If the retention time of an unknown DTG material is the same as, or very close to, that of a known diterpene glycoside, it is highly probable that they are the same. Slight differences sometimes occur between the retention time of diterpene glycosides chromatographically separated from plant extracts or extracts of other complex materials and the same glycosides chromatographed alone or in simple mixtures of substantially pure glycosides. Such differences are due to interactions of the components of the extracts (e.g., in the present invention DTG materials and accompanying impurities) with each other, with the stationary phase, with the eluent, and/or with any adventitious water present. An instance of such a shift of retention time is found in the data developed in Example 1, below.

The tentative identification of a diterpene glycoside from retention time comparisons may be confirmed by adding to the plant extract or other extract a sample of a known diterpene glycoside (the extract is "spiked" with the known glycoside) and chromatographing this new mixture under the same chromatographic conditions used for the initial identification. An increase in UV absorbance ("peak height") at the retention time associated with the tentatively identified glycoside further confirms its identity with the known glycoside.

Another method of confirming the identity of a chromatographically separated diterpene glycoside consists in isolating an eluate fraction containing it, removing the eluent, and then subjecting the glycoside to thin layer chromatography (TLC). The migration rate $R_f$ (=distance from origin to the center of the sample spot divided by distance from origin to solvent front) of the unknown glycoside is then compared with the $R_f$ values found when known individual diterpene glycosides are similarly chromatographed. When the $R_f$ of an unidentified diterpene glycoside is the same as that of a known diterpene glycoside, the two are generally considered to be identical. A further technique of establishing the identity of a glycoside by TLC is by "co-chromatographing" the known and unknown glycosides. In this technique, a sample of the unknown glycoside is placed on the TLC medium, then a sample of the known glycoside is placed on the same spot as the unknown, and then elution is carried out in the normal manner. The formation of a single, substantially round spot is generally considered positive evidence that the two glycosides are identical. (If the two glycosides were quite different, two spots would be observed. If there were only very slight differences between the two, the observed spot would tend not to be round.)

A method of distinguishing glycosides from non-glycosides by TLC arises from the fact that the chromatogram spots, in the TLC procedure used as described below, are made visible by a color-forming reaction with anisaldehyde-sulfuric acid reagent. It has been found that the color of glycoside spots usually is different from the color of non-glycoside spots, thus enabling glycosides to be readily distinguished from non-glycosides.

Using absorbance at 210 nm, the quantity of DTG in a sample may be determined from Beer's law standard curves. These curves are prepared by passing different quantities of known DTG materials through the chromatography column and measuring the resulting UV absorbances. In a typical chromatograph recorder trace, retention time is measured along the horizontal axis, UV absorbance along the vertical axis. Sharp separations are evidenced by distinct, well separated "peaks" of absorbance.

The following examples illustrate preferred embodiments of the invention. It will be understood that the invention is not limited to the proportions, materials, conditions, and procedures set forth in the examples, which are only illustrative.

In the examples, all proportions of mixed solvents are by volume, and all solvents are Fisher certified grade, obtainable from the Fisher Scientific Co., Pittsburgh, Pa.

EXAMPLE 1

A number of replicate runs were made to establish the conditions for recovery and separation of the diterpene glycosides stevioside, rebaudioside A, and rebaudioside C from *Stevia rebaudiana* plant material. In a typical run, dried (100° C., 1 hour in forced draft oven), powdered (30 mesh) *S. rebaudiana* leaves (0.5 gram) were continuously and sequentially extracted in a micro-soxhlet apparatus with chloroform (15 ml) for 3 hours (extract A) and then with methanol (15 ml) for 5 hours (extract B); the leaves then were refluxed with distilled water (15 ml) for 1 hour (extract C). Each extract was evaporated to dryness under vacuum, and the resulting residues were dissolved in chloroform (extract A residue, 10 ml), or in a solvent of 98% 1-propanol and 2% water (extract B residue, 50 ml; extract C residue, 25 ml) in preparation for chromatography.

The residues from extract A and extract C from certain runs were subjected to thin layer chromatography, using precoated silica gel $GF_{254}$ plates (20×20 cm, 0.25 mm thick; E. Merck, Darmstadt, G.F.R.) and developed with chloroform-methanol-water (30:20:1). After development, the chromatographs were air-dried, sprayed with anisaldehydesulfuric acid reagent and heated at 100° C. for 5 minutes to visualize DTG materials. No detectable quantities of the above-named diterpene glycosides were found in extract A or in extract C. (Since these glycosides are more soluble in water than in organic solvents, the results demonstrated that they were substantially completely extracted from the plant material in the methanol extraction.) The substantially complete removal of stevioside, rebaudioside A and rebaudioside C from the plant material by methanol was further confirmed by subjecting the extract C residues from certain of the extraction runs to the high performance liquid chromatography separation procedure which is described below. Using this procedure, no evidence was found of the presence of the above-named glycosides in the extract C residue.

High performance liquid chromatographic (HPLC) separations were conducted using a Waters Associates (Milford, Mass.) Model 600A liquid chromatograph equipped with a Rheodyne (Berkeley, Calif.) Model 7120 syringe-loading sample injector and 100 microliter sample loop, a Waters Associates Model 450 variable wavelength UV spectrophotometer, and a Texas Instruments (Houston, Tex.) Servo-Riter II portable recorder. The column used in the separation was composed of two Waters Associates 30 cm long×0.78 cm I.D. Protein I-125 columns arranged in series. Operating conditions for the separation were: ambient temperature; eluting solvent, Fisher certified grade 1-propanol, redistilled in glass to remove any high and low boiling impurities; solvent flow rate of 1 ml per minute; wavelength of UV detector, 210 nm; recorder chart speed of 3 inches per hour at 0.04 absorbance units full scale.

To obtain data for identification and quantitation of stevioside, rebaudioside A, and rebaudioside C, solutions containing known amounts of authentic samples of these materials were injected onto the column and their retention times and peak heights determined. Beer's law standard curves were obtained by injecting different quantities of stevioside (5, 10, 15, 20, 30, 50, 60, 80 and 100 micrograms per 100 microliter injection), rebaudioside A (5, 10, 20, 25, 50 and 100 micrograms per 100 microliter injection), and rebaudioside C (4, 6.25, 12.5, 20, 25, 50 and 100 micrograms per 100 microliter injection) onto the column in triplicate and measuring the resulting absorption peak heights. All of the glycosides gave linear detection responses at concentrations in the foregoing ranges.

Under the HPLC conditions used in this example, stevioside, rebaudioside C and rebaudioside A gave retention times of 43.2, 49.5 and 59.0 minutes, respectively (averaged results from replicate runs). For stevioside, rebaudioside C and rebaudioside A, Beer's law standard curves gave, respectively, slopes of 1.68, 1.22 and 0.91; Y axis (peak height) intercepts of $-1.16, +0.52$ and $+0.35$; and correlation coefficients of 0.999, 0.999 and 0.999, using linear regression analysis. The minimum detectable quantities were 1.0 microgram for stevioside and 2.0 micrograms for rebaudioside C and for rebaudioside A.

Glycosides recovered from the plant material in the extract B residue were separated from each other by the above-described HPLC procedure. In a typical separation, a 100-microliter quantity of a solution of the residue in a solvent of 98% 1-propanol, 2% water was chromatographed on the Protein I-125 column, employing 1-propanol as the eluent, as described above. Fractions of eluate showing peaks with retention times corresponding closely to those of stevioside, rebaudioside A and rebaudioside C were collected. FIG. 1 is a typical graph of such a chromatographic separation, with the UV absorbance of the eluate displayed on the vertical or Y-axis and retention time displayed on the horizontal or X-axis. The peaks numbered 1, 2, and 3 correspond, respectively, to stevioside, rebaudioside C and rebaudioside A. The graph illustrates the successful separation of these individual diterpene glycosides obtained from a plant extract. The peak for rebaudioside A, at approximately 62 minutes retention time, is displaced from the 59.0 minutes found when chromatographing a known sample of rebaudioside A alone or in a simple mixture of glycosides, for reasons such as discussed above.

The Protein I-125 column employed in the preferred embodiments of the invention has been used heretofore for the chromatography of other substances, employing eluents containing substantial proportions of water. It was found in the invention, on the other hand, that the combination of such a column and an organic solvent eluent containing very little or no water, i.e., substantially anhydrous, successfully resolved individual diterpene glycosides.

In certain of the runs, the identities of the diterpene glycosides associated with the several retention time peaks were confirmed by preparing three "spiked" mixtures of extract B residue; one spiked with stevioside, one with rebaudioside A and one with rebaudioside C. When these mixtures were chromatographed under the same conditions as used for the unspiked extract B residue, those peaks which were believed to correspond to stevioside, rebaudioside A and rebaudioside C were heightened when the spiking diterpene glycoside was, respectively, stevioside, rebaudioside A and rebaudioside C, thus confirming the identification of the peaks.

Another method for confirming the identity of the diterpene glycoside associated with a particular retention time peak was carried out with certain runs. Fractions of eluate each of which, from the UV absorbance data, appeared to contain substantially only one individual diterpene glycoside, were isolated. The eluent was removed from the fraction by evaporation to dryness, the residue was redissolved in 1-propanol/water, 98/2, and the solution was co-chromatographed with a sample of the authentic diterpene glycoside which it was believed the fraction contained. Using the TLC conditions described above, only a single spot was found on the chromatogram of each fraction. (Rf values for stevioside, rebaudioside C and rebaudioside A were, respectively, 0.30, 0.24 and 0.18). These results demonstrated that the fraction contained a diterpene glycoside in substantially pure form, and that the diterpene glycoside was identical with the diterpene glycoside with which it was co-chromatographed. It is difficult, with the TLC procedure described herein, to detect extremely small quantities of glycoside and, therefore, the corresponding eluate fractions from a number of replicate HPLC runs were collected and combined to obtain a quantity of glycoside large enough for ready identification by TLC.

In certain runs, the identities of individual diterpene glycosides were established by both the "spiking" and TLC methods. An aliquot of an extract B residue was chromatographed by the HPLC procedure described above, and other aliquots were then spiked and chromatographed similarly to establish the identity of the glycoside associated with a given peak. Still other aliquots were chromatographed by the above-described HPLC procedure, eluate fractions containing tentatively identified glycosides were collected, and the glycosides' identities were confirmed by the TLC procedure described above.

EXAMPLE 2

Employing the HPLC liquid chromatography system and conditions described in Example 1, standard solutions of authentic samples of rebaudiosides B, D and E, dulcoside A, and steviolbioside were chromatographed individually and their retention times determined.

Beer's law standard curves were obtained for each of the several glycosides by injecting samples of differing concentrations onto the column (dulcoside A, 0.5, 1, 5, 10 and 20 micrograms per 100 microliter injection; steviolbioside and rebaudioside B, 5, 10, 20, 40 and 80 micrograms per 100 microliter injection; and rebaudiosides D and E, 3.25, 7.5, 15, 30 and 60 micrograms per 100 microliter injection) in triplicate and measuring the resulting peak heights. All of the above glycosides gave linear detection responses when concentrations of 0.5-100 micrograms per 100 microliters were employed. Beer's law slopes, Y-axis (peak height) intercepts and correlation coefficients were determined by linear regression calculations and are shown together with retention times and minimum detectable amounts in Table 2, in order of increasing retention time. Data for stevioside, rebaudioside C and rebaudioside A, obtained as described in Example 1, are included also.

TABLE 2

| Diterpene Glycoside | Retention Time, Minutes | Minimum Detectable Amount, Micrograms | Slope | Y-Axis Intercept | Correlation Coefficient |
|---|---|---|---|---|---|
| DULCOSIDE A | 27.5 | 0.2 | 6.54 | +3.65 | 0.998 |
| STEVIOLBIOSIDE | 37.7 | 0.5 | 2.33 | +8.69 | 0.999 |
| REBAUDIOSIDE B | 40.9 | 0.5 | 1.55 | +20.52 | 0.995 |
| STEVIOSIDE | 43.2 | 1.0 | 1.68 | −1.16 | 0.999 |
| REBAUDIOSIDE C | 49.5 | 2.0 | 1.22 | +0.52 | 0.999 |
| REBAUDIOSIDE A | 59.0 | 2.0 | 0.91 | +0.35 | 0.999 |
| REBAUDIOSIDE E | 65.0 | 2.0 | 1.39 | +1.14 | 0.999 |
| REBAUDIOSIDE D | 84.0 | 2.0 | 1.29 | −3.18 | 0.998 |

Mixtures of the eight glycosides, including stevioside, steviolbioside, dulcoside A, and rebaudiosides A, B, C, D and E, were separated into their individual components by the HPLC procedure described in Example 1. In a typical run, a solution containing a mixture of the glycosides was prepared by placing from 1 to 5 mg of each of the glycosides in a 5 ml measuring flask, adding 0.15 ml of distilled water, warming on a water bath to about 55° C. for 10 minutes, and then adding several one-milliliter portions of 1-propanol, with warming after each addition. After dissolution of the glycosides, the flask was cooled and the volume of solvent adjusted to 5 ml with 1-propanol (the 1-propanol used was redistilled from glass). One hundred microliters of this solution was chromatographed.

A typical recorder trace of the UV absorbances of the eluate is shown in FIG. 2, where peak 1 corresponds to dulcoside A, peak 2 to steviolbioside, peak 3 to rebaudioside B, peak 4 to stevioside, peak 5 to rebaudioside C, peak 6 to rebaudioside A, peak 7 to rebaudioside E and peak 8 to rebaudioside D, in order of increasing retention time. The agreement of the retention times of these peaks with those foun for the glycosides individually demonstrated that the liquid chromatography system successfully separated the components of the mixture.

We claim:

1. A process for recovering diterpene glycosides from Stevia rebaudiana plant material, said process comprising:
sequentially extracting Stevia rebaudiana plant material with a first solvent of intermediate polarity to remove impurities therefrom in a first extract substantially free of diterpene glycosides, and then with a second solvent of high polarity to give a second extract containing diterpene glycosides;
chromatographing the resulting extracted diterpene glycosides on a liquid chromatography column having a packing comprising an oxygen-containing organic stationary phase covalently bonded through a silicon atom to an inorganic support;
said extracted glycosides being introduced onto said column for chromatography thereon in solution in said second solvent or in another solvent having a high polarity not substantially greater than the polarity of the second solvent;
said column being eluted with a solvent of polarity higher than that of said first solvent and lower than that of said second solvent; and
collecting individually eluate fractions rich in respective diterpene glycosides.

2. The process of claim 1 wherein, prior to being chromatographed, said extracted diterpene glycosides are freed of said second solvent and are dissolved in a third solvent of lower polarity than that of said second solvent for said introduction onto the column.

3. The process of claim 2 wherein said third solvent is comprised of 95-100% by volume of an alkanol of from two to four carbon atoms and the balance substantially water.

4. The process of claim 3 wherein said alkanol is 1-propanol.

5. The process of claim 1, 2, 3, or 4, wherein said first solvent is a liquid haloalkane of from one to four carbon atoms.

6. The process of claim 5 wherein said haloalkane is chloroform.

7. The process of claim 1, 2, 3 or 4, wherein said second solvent is an alkanol of from one to three carbon atoms.

8. The process of claim 1, 2, 3 or 4 wherein said second solvent is methanol.

9. The process of claim 1, 2, 3 or 4 wherein said eluting solvent is an alkanol of from two to four carbon atoms.

10. The process of claim 1, 2, 3 or 4 wherein said eluting solvent is 1-propanol.

11. The process of claim 1, 2, 3 or 4 wherein said stationary phase contains an ether oxygen and said support comprises a silica gel.

12. The process of claim 11 wherein said silica gel has a mean particle size diameter of about 5-15 microns and a mean surface area of about 100-500 square meters per gram.

13. The process of claim 11 wherein said stationary phase comprises a glycerylpropyl moiety.

14. A process for recovering diterpene glycosides from Stevia rebaudiana plant material, said process comprising:
sequentially extracting Stevia rebaudiana plant material with a first solvent comprising a liquid haloalkane of from one to four carbon atoms to remove impurities therefrom in a first extract substantially free of diterpene glycosides, and then with a second solvent comprising an alkanol of from one to three carbon atoms to give a second extract containing diterpene glycosides;
chromatographing the resulting extracted diterpene glycosides on a liquid chromatography column having a packing comprising an ether oxygen-containing organic stationary phase covalently bonded through a silicon atom to a silica gel support;
said extracted glycosides being introduced onto said column for chromatography thereon in solution in said second solvent or in another solvent having a high polarity not substantially greater than the polarity of the second solvent;

said column being eluted with an alkanol of from two to four carbon atoms; and collecting individually eluate fractions rich in the respective diterpene glycosides.

15. The process of claim 14 wherein said stationary phase comprises a glycerylpropyl moiety.

16. The process of claim 1, 2, 14 or 15 wherein said *Stevia rebaudiana* plant material comprises plant leaves.

17. A process for recovering diterpene glycosides from *Stevia rebaudiana* plant material, said process comprising:

sequentially extracting *Stevia rebaudiana* leaves with chloroform to remove impurities therefrom in a first extract substantially free of diterpene glycosides, and then with methanol to give a second extract containing diterpene glycosides;

chromatographing the resulting extracted diterpene glycosides on a liquid chromatography column having a packing comprising a glycerylpropyl moiety stationary phase covalently bonded through a silicon atom to a silica gel support having a mean particle size diameter of about 5–15 microns and a mean surface area of about 100–500 square meters per gram;

said extracted glycosides being introduced onto said column for chromatography thereon in solution in a solvent comprised of 95–100% by volume of 1-propanol and the balance substantially water;

said column being eluted with 1-propanol; and collecting individually eluate fractions rich in respective diterpene glycosides.

18. In a process for separating a mixture of diterpene glycosides of the *Stevia rebaudiana* plant by liquid chromatography on a packed column, the improvement which comprises employing as the column packing an oxygen-containing organic stationary phase covalently bonded through a silicon atom to an inorganic support.

19. The process of claim 18 wherein said stationary phase contains an ether oxygen and said inorganic support is silica gel.

20. The process of claim 19 wherein said stationary phase comprises a glycerylpropyl moiety.

21. The process of claim 19 wherein said silica gel has a mean particle size diameter of about 5–15 microns and a mean surface area of about 100–500 square meters per gram.

22. The process of claim 21 wherein said stationary phase comprises a glycerylpropyl moiety.

23. The process of claim 18, 19, 20, 21 or 22 wherein said column is eluted with an alkanol of from two to four carbon atoms.

24. The process of claim 18, 19, 20, 21 or 22 wherein said column is eluted with 1-propanol.

25. A process for separating a mixture of diterpene glycosides of the *Stevia rebaudiana* plant, said process comprising:

introducing a solution of said mixture of diterpene glycosides in a solvent onto a liquid chromatography column, said column having a packing comprising an oxygen-containing organic stationary phase covalently bonded through a silicon atom to an inorganic support;

said solvent comprising 95–100% by volume of an alkanol of from one to four carbon atoms and the balance substantially water;

eluting said column with an alkanol of from two to four carbon atoms; and collecting individually eluate fractions rich in respective diterpene glycosides.

26. The process of claim 25 wherein said stationary phase contains an ether oxygen.

27. The process of claim 25 wherein said stationary phase comprises a glycerylpropyl moiety.

28. The process of claim 26 wherein said inorganic support is silica gel.

29. The process of claim 28 wherein said stationary phase comprises a glycerylpropyl moiety.

30. The process of claim 25 wherein said stationary phase comprises a glycerylpropyl moiety and said support comprises a silica gel having a mean particle size diameter of from 5–15 microns and a mean surface area of from 100–500 square meters per gram.

31. The process of claim 25, 26, 27, 28, 29 or 30 wherein each of said alkanols is 1-propanol.

* * * * *

UNITED STATES PATENT AND TRADEMARK OFFICE
CERTIFICATE OF CORRECTION

PATENT NO. : 4,361,697
DATED : November 30, 1982
INVENTOR(S) : Robert H. Dobberstein and Mohamed S. Ahmed It is certified that error appears in the above-identified patent and that said Letters Patent are hereby corrected as shown below:

Column 2, lines 1 to 10, substitute the following formula:

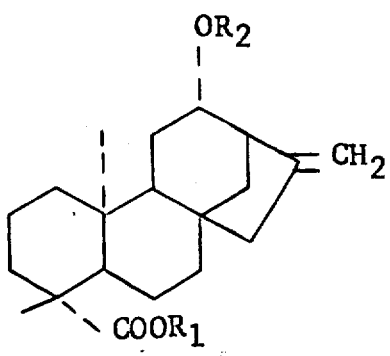

Column 8, line 52, change "anisaldehydesulfuric" to --anisaldehyde-sulfuric--.

Column 9, line 1, change "600A" to --6000A--.

Column 11, line 54, change "foun" to --found--.

Signed and Sealed this

Fifteenth Day of March 1983

[SEAL]

Attest:

GERALD J. MOSSINGHOFF

Attesting Officer   Commissioner of Patents and Trademarks